United States Patent [19]

Keen

[11] Patent Number: 4,579,983

[45] Date of Patent: Apr. 1, 1986

[54] PROCESS FOR THE HYDROLYSIS OF ALKYLENE OXIDES USING ORGANOMETALATES

[75] Inventor: Brian T. Keen, Charleston, W. Va.

[73] Assignee: Union Carbide Corporation, Danbury, Conn.

[21] Appl. No.: 594,267

[22] Filed: Mar. 28, 1984

[51] Int. Cl.[4] .................. C07C 31/20; C07C 33/26; C07C 35/14; C07C 33/035

[52] U.S. Cl. .................. 568/867; 568/811; 568/833; 568/857

[58] Field of Search ............... 568/867, 833, 811, 857

[56] References Cited

U.S. PATENT DOCUMENTS

| | | | |
|---|---|---|---|
| 4,160,116 | 7/1979 | Mieno et al. | 568/867 |
| 4,277,632 | 7/1981 | Kumazawa et al. | 568/700 |

FOREIGN PATENT DOCUMENTS 57-139026  2/1981  Japan .

73035  6/1981  Japan .................. 568/867

OTHER PUBLICATIONS

R. H. Wheaton, et al., "A Basic Reference on Ion Exchange", Kirk-Othmer, Encyc. of Chem. Tech., 2nd ed. vol. 11, pp. 871–899, (1966).
Dow Chemical Co., Dainex MSA-1 Anion Exchange Resin, T.D. Index 250.01, (undated).
USPA Ser. No. 594,256 (Docket 13955), filed 3/28/84.
USPA Ser. No. 594,268 (Docket 13947), filed 3/28/84.

*Primary Examiner*—J. E. Evans
*Attorney, Agent, or Firm*—Steven T. Trinker

[57] ABSTRACT

In processes for the hydrolysis of alkylene oxide to form alkylene glycols in the presence of selectivity-enhancing organometalate wherein the organometalate is provided in a water-insoluble phase, a stabilizing material is used to enhance the stability of the organometalate. The stabilizing material is water-soluble and comprises a cation and a selectivity-enhancing metalate anion.

30 Claims, No Drawings

PROCESS FOR THE HYDROLYSIS OF ALKYLENE OXIDES USING ORGANOMETALATES

This invention relates to processes for the production of alkylene glycols from alkylene oxides and water, which processes are conducted in the presence of selectivity-enhancing organometalates which are contained in a non-aqueous phase. In particular, the processes of this invention are capable of achieving enhanced selectivity to monoalkylene glycols over longer periods of time and can result in the production of higher quality glycol products.

INTRODUCTION TO THE HYDROLYSIS OF ALKYLENE OXIDE

Commercial processes for the preparation of alkylene glycols, for example, ethylene glycol, propylene glycol and butylene glycol, involve the liquid-phase hydration of the corresponding alkylene oxide in the presence of a large molar excess of water (see, for example Kirk-Othmer, *Encyclopedia of Chemical Technology*, Vol. 11, Third Edition, page 939 (1980)). The hydrolysis reaction is typically conducted at moderate temperatures, e.g., about 100° C. to about 200° C., with water being provided to the reaction zone in excess of 15 moles per mole of alkylene oxide. The primary by-products of the hydrolysis reaction are di- and polyglycols, e.g., dialkylene glycol, trialkylene glycol and tetra-alkylene glycol. The formation of the di- and polyglycols is believed to be primarily due to the reaction of alkylene oxide with alkylene glycol. As alkylene oxides are generally more reactive with alkylene glycols than they are with water, the large excesses of water are employed in order to favor the reaction with water and thereby obtain a commercially attractive selectivity to the monoglycol product.

Since the alkylene glycols must be recovered from the hydrolysis reaction mixtures, the large excess of water can result in an energy intensive procedure. Typically, the water is removed by evaporation to leave an alkylene glycol-containing residue which is purified by distillation. Hence, a reduction in the amount of water employed while maintaining, or enhancing, selectivity toward the monoglycol product could be beneficial from the standpoint of energy efficiency.

Not only is the monoglycol product often the desired product for the hydrolysis of alkylene oxides but also many of the applications for monoglycols are demanding in the quality of the monoglycol product. For instance, monoethylene glycol is used in the preparation of polyesters (polyethylene terephthalate) and must meet rigid standards so as not to adversely affect the properties of the finished polyesters, e.g., fiber or film. Typical polyester grade monoethylene glycol must meet the specifications set forth in Table I:

TABLE I

| Representative Polyester Grade Specifications | |
|---|---|
| Specific Gravity (20/20° C.) | 1.1151–1.1156 |
| Distillation, 760 mm | |
| Ibp, °C. min. | 196 |
| Dp, °C. max. | 200 |
| Acidity, % by wt., as HAc max. acid | 0.005 |
| UV Transmittances  Wavelength (mμ) | Transmittance (%, min.) |
| 220 | 70 |
| 275 | 90 |

TABLE I-continued

| Representative Polyester Grade Specifications | |
|---|---|
| | 350    98 |
| Iron, ppm max. | 0.07 |
| Chlorides | none by test |
| Diethylene glycol, % by wt., max. | 0.08 |
| Water, % by wt., max. | 0.08 |
| Water solubility at 25° C. | miscible, all proportions |
| Ash, gm/100 ml, max. | 0.005 |
| Color, Pt—Co, max. | 5 |
| Odor | mild, practically none |
| Suspended matter | substantially free |

Accordingly, interest exists in assuring that the alkylene glycol product from the hydrolysis process can be readily refined to obtain the desired, high quality product. Any effort to enhance the yield of monoalkylene glycol, e.g., by the use of catalysts, is also viewed from the standpoint of the effect on the quality of the hydrolysis and any additional costs involved in refining the monoalkylene glycol to meet any demanding specifications for the product.

Previously, numerous catalysts have been proposed to enhance the selectivity of the hydrolysis reaction to monoalkylene glycol.

For example, U.S. Pat. No. 4,277,632, issued July 7, 1981, discloses a process for the production of alkylene glycols by the hydrolysis of alkylene oxides in the presence of a catalyst of at least one member selected from the group consisting of molybdenum and tungsten. The patent discloses that the catalyst may be metallic molybdenum or metallic tungsten, or inorganic or organic compounds thereof, such as oxides, acids, halides, phosphorous compounds, polyacids, alkali metal and alkaline earth metal, ammonium salts and heavy metal salts of acids and polyacids, and organic acid salts. An objective of the disclosed process is stated to be the hydrolysis of alkylene oxides wherein water is present in about one to five times the stoichiometric value without forming appreciable amounts of by-products such as the polyglycols. The reaction may be carried out in the presence of carbon dioxide; however, when the reaction is carried out in the presence of nitrogen, air, etc., the patentees state that the pH of the reaction mixture should be adjusted to a value in the range of 5 to 10. Japanese Kokai No. JA 54/128,507, published Oct. 5, 1979, discloses a process for the production of alkylene glycols from alkylene oxides and water using metallic tungsten and/or tungsten compounds.

Japanese Kokai No. JA 56/073,035, published June 17, 1981, discloses a process for the hydrolysis of alkylene oxide under a carbon dioxide atmosphere in the presence of a catalyst consisting of a compound containing at least one element selected from the group of titanium, zirconium, vanadium, niobium, tantalum and chromium. The compounds include the oxides, sulfides, acids, halides, phosphorous compounds, polyacids, alkali metal salts of acids and polyacids, ammonium salts of acids and polyacids, and heavy metal salts of acids.

Japanese Kokai No. JA 56/073,036, published June 17, 1981, discloses a process for the hydrolysis of alkylene oxide under a carbon dioxide atmosphere in the presence of a catalyst consisting of a compound containing at least one element selected from a group comprising aluminum, silicon, germanium, tin, lead, iron, cobalt and nickel.

U.S. patent applications Ser. Nos. 428,815, filed Sept. 30, 1982, (now abandoned) and 530,235, filed Sept. 8, 1983, of J. H. Robson and G. E. Keller, disclose the production of monoalkylene glycols with high selectivity by the reaction of a vicinal alkylene oxide with water in the presence of a water-soluble vanadate. Hence, lower water to alkylene oxide ratios can be employed using the disclosed process with attractive selectivities to the monoglycol products. The counter ion to the vanadate is selected to provide a water-soluble vanadate salt under the reaction conditions employed and alkali metals, alkaline earth metals, quaternary ammonium, ammonium, copper, zinc, and iron are suggested cations. It is also disclosed that the vanadate may be introduced into the reaction system in the salt form or on a support such as silica, alumina, zeolites and clay. Since the vanadate ion is water soluble, it can be lost from the reaction system and means must be provided to recover it from the effluent from the reaction zone.

Several processes have been provided wherein a selectivity-enhancing metalate anion-containing material is contained in a non-aqueous phase during the hydrolysis process.

These selectivity enhancing metalate anions are in association with organic-containing cations or electropositive complexing sites (herein referred to as organometalates).

Copending U.S. patent application Ser. No. 594,385, filed on even date herewith, of J. R. Briggs and J. H. Robson, is directed to processes for the hydrolysis of alkylene oxides in a reaction menstruum comprising two phases, an aqueous phase and a substantially water-insoluble liquid phase in which the concentration of a selectivity-enhancing metalate anion-containing material (which may be an organometalate) is greater in the water-insoluble phase than in the aqueous phase. Advantageously, the alkylene glycol product is preferentially soluble in the aqueous phase and the recovery of the metalate anion-containing material from the product is facilitated by the ability to use phase separation.

Copending U.S. patent application Ser. No. 594,256, filed on even date herewith, of J. R. Briggs, G. L. O'Connor, and J. H. Robson, is directed to processes for the hydrolysis of alkylene oxides in which alkylene oxide and a selectivity enhancing, dissociatable metalate anion (which may be an organometalate) are contacted in the relative absence of water under conditions sufficient to associate at least a portion of the alkylene oxide with the metalate anion and then the associated material is contacted with water to form alkylene glycol. In embodiments of the invention, virtually all the produced alkylene glycol is monoalkylene glycol.

Copending U.S. patent application Ser. No. 594,268, filed on even date herewith, of R. D. Best, J. A. Collier, B. T. Keen and J. H. Robson, is directed to processes for the hydrolysis of alkylene oxide in the presence of selectivity-enhancing metalate anion which is in association with electropositive complexing sites on a solid support. Often, the electropositive complexing sites contain hydrocarbyl moieties and are thus encompassed within the group of organometalates as the term is defined for purposes herein. Because the metalate anion is in association with a complexing site on a solid, the recovery of metalate anion from glycol product can be effected by phase separation. Readily available solids include anion exchange resins.

Patent application Ser. Nos. 594,385, 594,256 and 594,268 are herein incorporated by reference.

The usefulness of organometalates is to some extent determined by their stability in the reaction medium and during their recoveries, particularly when continuous operations in which reuse of the metalate is desired. Organometalates may exhibit instability, for instance, by being displaced from the organo-containing cation with which they are associated, by reduction of the metalate anion, and/or by degradation of the organo-containing cation. The instability not only affects the availability of active organometalate, but also the degradation products (particularly of the organo-containing cation) can adversely affect the quality of the hydrolysis product. For example, a styrene-divinylbenzene anion exchange resin with quaternary ammonium substituents is subject to degradation by loss of the ammonium functionality and by degradation of the polymer.

In processes in which the selectivity-enhancing metalate anion is provided in a non-aqueous phase, once the metalate anion is displaced from the organometalate, it can be lost from the reaction system with the removal of the aqueous phase. The remaining organic-containing cation may be more subject to degradation.

The propensity of, for example, anion exchange resins to degrade is hinted at in the prior art. Japanese Kokai No. JA 57/139,026, published Aug. 27, 1982, discloses a process for the hydrolysis of alkylene oxides in the presence of carbon dioxide and a halogen-type anion exchange resin as a catalyst. The exemplified catalyst is a chlorine-type anion exchange resin (Dowex MSA-1(TM), a product of The Dow Chemical Company) and a similar iodine-type anion exchange resin. At a mole ratio of alkylene oxide to water of about 0.66, the selectivity to monoethylene glycol was reported to be 91.0 percent using the chlorine-type anion exchange resin and 89.6 percent using the iodine-type anion exchange resin. In the absence of carbon-dioxide, the application disclosed that a selectivity to the monoethylene glycol of 34.8 percent was obtained and an unpleasant smell was noted in the product. In the absence of any anion exchange resin and in the presence of carbon dioxide, the selectivity to monoethylene glycol was reported to be 37.5 percent. All of the examples were conducted in an autoclave immersed in an oil bath at a temperature of 150° C. The disclosure reports that the maximum reaction liquid temperature was 130° C. and the reaction was carried out for 90 minutes. While the application did not specifically indicate the source of the unpleasant smell which originated in the comparative example where the carbon dioxide atmosphere was not employed, it could be the result of degradation of the anion exchange resin.

Furthermore, literature on various anion exchange resins often points to the limits of thermal stability of ion-exchange materials. For illustration, R. H. Wheaton, et al., in "A Basic Reference on Ion Exchange", Kirk-Othmer, *Encyclopedia of Chemical Technology*, Second Edition, Volume 11, pages 871 to 899, (1966) state at page 885:

"The limits of thermal stability are improved by the strength of the C—N bond in the case of anion resins. This strength is quite sensitive to pH, a low pH favoring enhanced stability. The quanternary ammonium salts are the least stable, with a temperature limitation of 50° C. often recommended for hydroxide cycle operations. The tertiary amines are the most stable; good performance may be maintained at 100° C."

Dowex MSA-1 (TM) anion exchange resins available from Dow Chemical Company are noted by their manufacturer (undated brochure bearing the identification. "T.D. Index 250.01") to have a maximum operating temperature in the hydroxyl form of 140° F. (60° C.) and in the chloride form of 300° F. (150° C.).

Usually, the degradation of the organic-containing cation can be mitigated by using lower processing temperatures. However, this reduces the rate of reaction and provides less available heat for heat integration in a hydrolysis plant, e.g., the heat may be desired for evaporation or distillation operations for the recovery of glycol products.

Without being restricted to theory, it is believed that the degradation of the organic-containing cation is due to an attack which is promoted by anions, e.g., hydroxide, chloride, etc. Thus, selectivity-enhancing metalate anions would also be expected to be deleterious to organic-containing cations.

Accordingly, processes are sought in which organometalates can be employed at advantageous temperatures for effecting the hydrolysis of alkylene oxide on a commercial basis yet minimize the degradation of the organometalates.

OVERVIEW OF THE INVENTION

By this invention, processes are provided that enhance the attractiveness of using organometalates contained in a non-aqueous phase in processes for the hydrolysis of alkylene oxide to form alkylene glycols with enhanced selectivity to monoalkylene glycols. In accordance with this invention, a stabilizing material is provided in the presence of the organometalate wherein the stabilizing material comprises a cation and a selectivity-enhancing metalate anion and is preferably more soluble in water under the hydrolysis conditions than the organometalate. The stabilizing material, which may be present in very small amounts based on the reaction menstruum, e.g., frequently less than the 0.1 weight percent, can reduce the amount of degradation of the organometalate under given hydrolysis conditions.

This invention is particularly advantageous for use in hydrolysis processes in which the organometalate is subject to degradation. For example, with anion exchange resins that have, say, quaternary ammonium or protonated tertiary amine functionality, the rate of loss of activity is evidenced by decreasing selectivity to the monoethylene glycol. The reduction in selectivity can be reduced using processes in accordance with this invention. Thus, the processes of this invention provide for longer periods of operation than could heretofore be expected.

Moreover, the quality of the hydrolysis product is often improved thereby facilitating obtaining commercially-acceptable monoalkylene glycol product. In part, because the stabilizing material is effective in small quantities, it often has little effect on the ultimate monoalkylene glycol product quality.

Further, the stabilizing material can be selected on the basis of avoiding unduly adverse effects on the glycol product quality. Hence, considerably greater flexibility exists in the selection of the stabilizing material and factors such as cost of the stabilizing material can be readily accommodated in making the selection.

DISCUSSION OF THE ORGANOMETLATES

The alkylene oxide and water are contacted with an organometalate which comprises a selectivity-enhancing metalate anion in association with electropositive complexing sites on an organic-containing cation wherein the organometalate is contained in a non-aqueous phase.

The metalates are characterized by an anionic structure containing at least one polyvalent metal atom, M, having a positive functional oxidation state, e.g., often an oxidation state of at least +3, usually +4 to +7, and at least one oxygen ligand usually characterized as a double bonded oxygen atom. The metalate anion can be illustrated by the following formula:

wherein q is the negative charge of the anion, which is usually between −1 and −4, A is one or more substituents to fill the remaining valencies (m) of M, and may be the same or different and may be, for instance, double-bonded oxygen; halogen (e.g., chlorine, fluorine, iodine); —O— or —S— wherein the remaining valency of the oxygen or sulfur atom is in free ionic form or is bonded to a metal atom (as in a bimetal or polymetal-containing metalate) or a counter ion, e.g., alkali metal, alkaline earth metal, ammonium, phosphonium and the like cations; or an organic radical, e.g., alkyl, aryl, acyl, alkoxy, amino, phosphino, etc. of 1 to about 12 carbons; and the like. Most commonly A is —O— or =O. Even when the A in the starting organometalate is other than —O—, e.g., chlorine, it is possible that the original substituent becomes replaced by —O— in the course of the process.

Particularly preferred metals for the metalate anions include the metals in groups Vb and VIb of the periodic chart such as vanadium, molybdenum and tungsten, although other metals may also find application. Representative metalate anions which are especially useful include molybdate, tungstate, metavanadate, hydrogen pyrovanadate and pyrovanadate (although because of the complex chemistry associated with many metalate anions, the precise structure of the operative specie or species may be different). Frequently, the metalate anion comprises at least one anion conventionally characterized by the formulae $[MoO_4]^{2-}$, $[VO_3]^-$, $[V_2O_7H]^{3-}$, $[V_2O_7]^{4-}$, and $[WO_4]^{2-}$; however, it is recognized that the chemistry of these metalate anions, particularly the vanadates, is complex, and the exact chemical formula under the conditions of the process may prove to be different.

Not all metalate anions, including those of vanadium, tungsten and molybdenum, exhibit desired activity with alkylene oxide. For example, paramolybdate and paratungstate anions (as the metalate anion added) appear to exhibit little, if any, activity for enhancing selectivity.

However, in an aspect of the invention, the metal for the metalate anion is selected on the basis of its nucleophilicity and electrophilicity as in the metalate with respect to alkylene oxide. For example, the metal as in the metalate often has a nucleophilicity with respect to ethylene oxide greater than that exhibited by rhenium as rhenate anion under the same conditions. Also, it is frequently the case that the metal as the metalate has an electrophilicity with respect to ethylene oxide greater than that exhibited by vanadium in orthovanadate (as that species) under the same conditions.

A particularly convenient method for approximating nucleophilicity and electrophilicity characteristics of a metal in a metalate anion is by comparing the rate and selectivity to monoethylene glycol under substantially the same hydrolysis conditions but employing an equimolar amount (based on the anion) of the subject metalate anion and the reference anion. For the sake of ease, the cation may be sodium. If the rate and/or selectivity to the monoethylene glycol is less than that provided by the rhenate anion, then the metal as the metalate is probably less nucleophilic than rhenate with respect to ethylene oxide. If the production of diethylene glycol and polyethylene glycol is greater than that provided with orthovanadate, regardless of the rate of formation of glycols, then the metal as the metalate is probably less electrophilic than orthovanadate with respect to ethylene oxide.

Because the selectivity-enhancing metalate anions enhance the selectivity of the hydrolysis to the monoalkylene glycol product, it is believed that an interaction or even chemical reaction occurs between the metalate anion and the alkylene oxide. See, for example, copending U.S. patent application Ser. No. 594,264, filed on even data herewith, of J. R. Briggs and J. H. Robson, herein incorporated by reference. Any intermediate species formed between the metalate anion and alkylene oxide is believed to hydrolyze more rapidly than the rate at which it is formed. Thus, in the presence of water, the chemical determination of any intermediate species through techniques such as nuclear magnetic spectroscopy, is not presently feasible. Without being limited to theory, it is believed that advantageous metalate anions are those that are capable of interacting or reacting with alkylene oxide.

The processes of this invention involve the existence of a non-aqueous phase containing organometalate during the hydrolysis reaction. The non-aqueous phase may be liquid or solid. The cation is substantially inert to water, alkylene oxide and alkylene glycol, and the preferred cations are those whose degradation products do not adversely affect the quality of alkylene glycol or can facilely be removed from the alkylene glycol product.

The metalate anions are associated with a cation and are dissociatable from the cation. Although the cations may be substantially insoluble, or have little solubility, in water at reaction conditions, the metalate anion can provide the enhanced selectivity of monoalkylene glycol. However, if the metalate anion is too tightly bound, it will not have the desired activity. Thus, calcium vanadate, which has little solubility in water and retains the metalate anion tightly bound, has not been found to be an acceptable metalate-containing compound. On the other hand, where the cation is, for instance, as essentially insoluble quaternary ammonium moiety, the dissociatable nature of the metalate anion is believed to permit its usefulness to achieve enhanced selectivities to monoalkylene glycol.

In accordance with the aspects of the invention in which the non-aqueous phase is liquid, the cation renders the organometalate preferentially soluble in an organic medium as compared to water. Often, the organometalate will have a greater solubility in a given water-immiscible organic solvent such as toluene than in distilled water at a given temperature, say, 25° C. In some instances, the solubility coefficient is at least about 5 times, say, at least about 20 times, greater in toluene than the solubility in distilled water at 25° C. Sometimes the organometalate is substantially insoluble in distilled water, e.g., less than about 50, say, less than 10, grams of the organometalate will dissolve in one liter of water at 25° C. Some organometalates are immiscible with water and some are solid at ambient temperatures, for instance, 25° C., or even at temperatures often used for hydrolysis, e.g., about 50° to 250° C., although they are capable of being dissolved in an organic solvent.

Organometalates may be represented by the formula:

$$[(R^0)_m Y_n]^{x+} \; [L^{x+'}]_{z-1} \; [(A)_q M]^{a-} \qquad \text{I.}$$

wherein $[(R^0)_m Y_n]^{x+}$ is an organo-containing cation having a positive charge of x and Y is a polyvalent element, which is an ionic charge carrying center, $R^0$ is hydrogen or hydrocarbyl-containing substituent with the proviso that the organo-containing cation has at least one $R^0$ which contains a hydrocarbyl substituent, m is the average number of electron pairs shared by Y with the total $R^0$ groups, n is the number of charge carrying centers, wherein m, n and x are related by the equation $x = n\,(V-m)$ in which V is the average functional oxidation state of Y wherein each electron pair used by each Y in bonding to $R^0$ is given the value of 1 and the functional oxidation state of Y is the sum of the electron pairs bonding to $R^0$ and $x/n$, wherein x is an integer of 1 or 2; wherein L is a cation which has a positive charge of $x'$ and which may be the same or different from the organo-containing cation, where $x'$ is usually 1 or 2; wherein z is the number of organo-containing cations which is from 1 to 3. Hence, the negative charge, a, of the metalate anion equals the amount of $x + [(z-1)(x')]$.

The hydrocarbyl-containing substituents useful in the organo-containing cation frequently contain at least four carbon atoms, and may be further substituted with moieties that are not reactive with the anion.

L may be any suitable cation and often is another organo-containing cation or a non-organo-containing cation which serves to balance the charge of the anion. L may include alkali metals, alkaline earth metals, copper, zinc, iron, ammonium cations, phosphonium cations, sulfonium cations, and other cations including organic-containing cations, e.g., containing alkyl, alkoxy, acyl, aryl, amino, phosphino, etc., groups of 1 to about 12 carbons.

Suitable cations may include structures represented by the formulae:

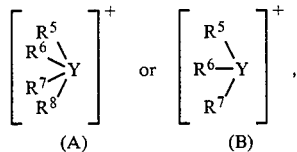

where Y is nitrogen, phosphorous, or arsenic for formula A, or sulfur for formula B, i.e., ammoniums, phosphoniums, arsoniums and sulfoniums, where each of $R^5$, $R^6$, $R^7$ and $R^8$ may be the same or different and may combine to form cyclic structures. Exemplary of each of $R^5$, $R^6$, $R^7$ and $R^8$ are hydrogen and unsubstituted and substituted hydrocarbyls of 1 or more carbon atoms, e.g., to about 70 carbon atoms. Representative cations are disclosed in U.S. patent application Ser. No. 594,264.

Organo-containing cations which may be useful include the bis(hydrocarbyl-phosphine) iminiums represented by the formula $$[(R_3^9 P)_2 N]^+$$

wherein each $R^9$ may be the same or different and may be the same as set forth for $R^5$ to $R^8$. Illustrative iminiums are disclosed in Ser. No. 594,264.

Illustrative of the organo-containing cations are tetrahydrocarbyl ammoniums, e.g., tetramethyl ammonium, tetraethyl ammonium, tetra-n-propyl ammonium, tetra-n-butyl ammonium, tetra-isobutyl ammonium, trimethyl butyl ammonium, tetraheptyl ammonium, tetraphenyl ammonium, tetrabenzyl ammonium, tetradodecyl ammonium, tetraoctadecyl ammonium, and the like; trihydrocarbyl ammonium, e.g., trimethyl ammonium, triethyl ammonium, triphenyl ammonium, tridodecyl ammonium, trioctadecyl ammonium, and the like; dihydrocarbyl ammoniums, e.g., dimethyl ammonium, diethyl ammonium, di-n-butyl ammonium, di-n-heptyl ammonium, diphenyl ammonium, dibenzyl ammonium, didodecyl ammonium, dioctadecyl ammonium, and the like; hydrocarbyl ammoniums, e.g., methyl ammonium, n-butyl ammonium, dodecyl ammonium, octadecyl ammonium, phenyl ammonium, benzyl ammonium, and the like; tetrahydrocarbyl phosphoniums, e.g., tetramethyl phosphonium, tetraethyl phosphonium, tetra-n-propyl phosphonium, tetra-n-butyl phosphonium, tetra-isobutyl phosphonium, trimethyl butyl phosphonium, tetraheptyl phosphonium, tetraphenyl phosphonium, tetrabenzyl phosphonium, tetradodecyl phosphonium, tetraoctadecyl phosphonium, and the like; trihydrocarbyl phosphonium, e.g., trimethyl phosphonium, triethyl phosphonium, triphenyl phosphonium, tridodecyl phosphonium, trioctadecyl phosphonium, and the like; dihydrocarbyl phosphoniums, e.g., dimethyl phosphonium, diethyl phosphonium, di-n-butyl phosphonium, di-n-heptyl phosphonium, diphenyl phosphonium, dibenzyl phosphonium, didodecyl phosphonium, dioctadecyl phosphonium, and the like; hydrocarbyl phosphoniums, e.g., methyl phosphonium, n-butyl phosphonium, dodecyl phosphonium, octadecyl phosphonium; phenyl phosphonium, benzyl phosphonium, and the like; bis(hydrocarbyl phosphine)iminiums such as bis(triphenyl-phosphine)iminium, bis(tribenzyl-phosphine)iminium, bis(trimethylphosphine)iminium, bis(tridodecyl-phosphine)iminium, and the like; quaternized diamines such as N,N'-bis(trimethyl)propylene diamine, N,N'-bis(triphenyl)propylene diamine, N,N'-bis(trioctadecyl)propylene diamine; and quaternized diphosphines such as P,P'-bis(trimethyl)propylene diphosphine, and the like.

When the non-aqueous phase containing the metalate anion is solid, the metalate anion is in association with electropositive complexing sites on a water-insoluble support which may be organic or inorganic, i.e., the support is solid under the conditions of the reaction. The electropositive complexing sites and the water-insoluble support are substantially non-reactive with water, alkylene oxide and alkylene glycol. Typical electropositive complexing moieties can contain strongly electropositive complexing groups such as quaternary ammonium groups, quaternary phosphonium groups, sulfonium groups, or arsonium groups or moderately electropositive complexing groups such as protonated tertiary amines and protonated tertiary phosphines. Because of the stability and availability of quaternary ammonium and protonated tertiary amine groups, they are generally preferred.

Suitable electropositive complexing groups include those having the general formula:

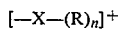

wherein X is nitrogen, phosphorous, sulfur, or arsenic bonded directly or indirectly to the support; and R may be the same or different and is hydrogen monocyclic aryl or aralkyl of 6 to 8 carbon atoms, monocyclic alkaryl of 7 to 9 carbon atoms, or alkyl or alkoxy of 1 to about 6 carbon atoms, and R may be substituted with groups which are substantially non-reactive with alkylene oxide, akylene glycol, or water, e.g., hydroxy groups such as hydroxyalkyl substituents, haloalkyl substituents, silyl substituents, siloxy substituents, and the like; and n designates that sufficient R groups are provided to satisfy the remaining valencies of X, e.g., n is 3 and X is nitrogen when the electropositive complexing site is a quaternary ammonium. Frequently, the stability of the electropositive complexing sites is enhanced when R is lower alkyl, especially methyl. It is also possible for X to be contained in a heterocyclic structure. For example, such cyclic structures contain 5 or 6 ring members with one or two members being the charge-carrying center X.

The electropositive complexing site may be bonded to the solid support through, for example, an alkylene, arylene, silyl or siloxy group.

Solid supports having electropositive complexing sites include inorganic substrates, such as carbon, silica gel, zeolite clay and glass beads. These supports may have the electropositive complexing sites affixed through adsorption, reaction or graft polymerization. See, for instance, Japanese Kokai Nos. 50/32085 and 52/26386. See also, P. Tundo, et al., "Anion-Exchange Properties of Ammonium Salts Immobilized on Silica Gel," J. Am Chem. Soc., Vol. 104, pp 6547–6551 (1982), and P. Tundo, et al., "Phase-Transfer Catalysts Immobilized and Adsorbed on Alumina and Silica Gel", J. Am. Chem. Soc., Vol 104, pp 6551–6555 (1982). U.S. Pat. No. 4,430,496 discloses silyl alkylammonium sites on inert particles. See also German patent application No. 2,433,409. The above are all herein incorporated by reference.

Suitable supports for the electropositive complexing sites also include water-insoluble anionic resins. The resin can be varied to convenience and can comprise essentially any resinous composition. The resins include high molecular weight polymers and copolymers, e.g., addition and condensation polymers, including polyalkylenes, polyesters, polycarbonates, polysulfones, polyimides, phenolic resins, formaldehyde resins, polyurethanes and the like, and the electropositive complexing sites may be adsorbed, reacted or grafted on the resin. While many available resins are carbon-based, silica-based resins may also find application in processes in accordance with this invention. These resins include organosiloxane polymers, such as dimethyl polysiloxane, methylphenyl polysiloxane, methylvinyl polysiloxane, cyanoalkylmethyl polysiloxanes and fluoroalkylmethyl polysiloxanes. See, for example, U.S. Pat. No. 4,417,066, issued Nov. 22, 1983, pertaining to organosiloxane polymers containing quaternary ammonium sites. U.S. Pat. No. 4,410,669 discloses polymeric ammonium compounds with a silica-type backbone which are said to exhibit good thermal stability and inertness to chemical attack. Both of these patents are herein incorporated by reference.

Monomers which can be employed in preparing carbon-based resins include styrene and styrene derivatives such as methylstyrene, ethylstyrene, vinylnaphthalene, 3,4,6-trimethylstyrene, chlorostyrene, methoxystyrene, N,N-dimethylaminostyrene, nitrostyrene, chlorostyrene, trifluorostyrene, trifluoromethylstyrene and aminostyrene; butadiene; acrylonitrile and acrylonitrile derivatives; acrylic acid and acrylates such as methyl acrylate and chloromethyl acrylate; methacrylic acid and methacrylates such as cyclohexyl methacrylate, dimethylaminoethyl methacrylate, glycidyl methacrylate and methyl methacrylate; maleates such as diethyl maleate; fumarates such diethyl fumarate; vinyl ketones such as methyl vinyl ketone and ethyl isopropyl ketone; vinylidenes; acrylamide and acrylamide derivatives; aliphatic acid vinyl esters such as vinyl acetate, vinyl butylate and vinyl caproate; formaldehyde with, e.g., phenol, xylene, urea, melamine; bisphenol A; sulfones such as dichlorodiphenyl sulfone; phosgene; toluene diisocyanate; polyols such as ethylene glycol; epoxybutadiene; etc.

For purposes of strength and chemical resistance, the resin is preferably cross-linked. Representative resins which can be cross-linked include styrene-divinylbenzene, styrene-glycol dimethacrylate, aniline-formaldehyde, aryl polyamine-formaldehyde, phenol-formaldehyde, polyacrylate, and the like. Generally, the amount of cross-linking agent provided is an amount of about 4 or 5 to 30 or 40 mole percent based on the monomer used to prepare the resin.

Cross-linking agents which can be employed in preparing resins include divinylbenzene, divinyltoluene, divinylnaphthalene, divinylethylbenzene, trivinylbenzene, divinyldiphenylmethane, divinylbenzyl, divinylsulfone, divinylketone, bis(vinylpyridinoethyl) ethylene diamine, diallyl phthalate, triallylamine, N,N'-ethylenediacrylamide, ethylene glycol dimethacrylate, triethylene glycol dimethacrylate, trimethylolpropane trimethacrylate, trimethylolpropane triacrylate, triallyl isocyanurate and diallyl melamine.

The resins can take many forms, such as swellable gels, semi-porous or iso-porous resins, or macro-porous (macro-reticular) resins. The resins may be spherical or irregular granules which in turn may be supported on a larger solid structure. Frequently, the major dimension of the resins is about 0.1 to 5 millimeters (e.g., 0.3 to 1 or 2 millimeters).

Anion exchange resins having quaternary amine sites and tertiary amine sites are commercially available. These resins include resins with acrylic matrices such as Amberlite (TM) IRA-68, IRA-60, and XE-258 resins available from Rohm & Haas Co.; phenolic-containing matrices such as Amberlite (TM) IRA-4B resin available from Rohm & Haas Co.; styrene-divinylbenzene matrices such as Amberlite (TM), IRA-900, IRA-904, IRA-93, IRA-94, and IRA-400 resins available from Rohm & Haas Co., Dowex (TM) 1, 2, 11, WGR, MSA-1, and MWA-1 resins available from the Dow Chemical Company, and Duolite (TM) A-101, A-102, and A-114, available from the Diamond Shamrock Corp.

Preferably, the support has at least about 0.1 e.g., 0.5 to 10, say 0.5 to 5 milli-equivalents of exchange capacity (based on the pendant electropositive complexing sites) per gram of dry support. It is at these sites that the association occurs between the metalate anion and the insoluble support.

The association of the metalate with the electropositive complexing sites on the insoluble support may be provided in any convenient manner. Usually the placing of the metalate on the insoluble support is accomplished by a loading technique whereby a soluble metalate salt is contacted in solution in an inert liquid medium with the insoluble support to displace original anion at the site. The counter ions to the metalates useful in preparing the solid supported metalates used in this invention are preferably water soluble, include alkali metals, alkaline earth metals, ammonium ion, copper, zinc, iron, quaternary ammonium cations, quaternary phosphonium cations, sulfonium cations, and other cations. Inert liquid media include water, aliphatic and aromatic hydrocarbons and substituted hydrocarbons such as hexane, benzene, toluene, xylene, o-dichlorobenzene, methylene chloride, chloroform, carbon tetrachloride, and the like.

The loading can occur at any temperature at which the metalate is dissolved. The temperature employed is preferably below that which results in unduly adverse effects to the reactants. Usually, the temperature will be about 0° C. to 120° C., say, about 15° C. to 100° C. Any convenient pressure may be employed, and subatmospheric pressures may assist in the dispersion of the metalate anion throughout the suppport. The loading process is typically conducted under a suitable atmosphere which frequently may be a substantially inert atmosphere, such as air or nitrogen, for a sufficient period of time to enable desired amounts of metalate anion to become associated with the electropositive complexing sites. This period of time will generally vary with the method, reagents and conditions employed, but it will often be about 0.5 to 50, say about 1 to 15 hours. The resulting product containing the metalate may be recovered by any convenient physical separation technique, such as filtering, decanting and evaporating.

In order to obtain the desired metalate in association with the electropositive complexing sites on the insoluble support, it is not necessary to use the metalate form. Indeed, any form of the metal which will yield the metalate by reaction subsequent to the loading, including in situ during the hydrolysis reaction, is believed to be suitable. The metal-containing anions may therefore contain halide, e.g., chloride and iodide; sulfide, aliphatic or aromatic hydrocarbon, or similar substituents. The selection of the metalate or precursor of the metalate will, in general, be dependent upon the availability of the compound and its processing characteristics in order to form the association with the electropositive complexing sites of the insoluble support and, in the case of the precursors to the metalate, the ability to form the desired product.

Typically during loading, the mole ratio of metalate ion to the electropositive complexing sites is between about 1:100 to about 100:1, and frequently is between about 1:1 to 25:1. In the prepared product with the associated metalate anion, the ratio of electropositive complexing sites having associated metalate anion to total electropositive complexing sites is frequently between about 1:10 to 1:1, preferably about 0.9:1 to 1:1. It has generally been noted that even though the metalate anion may have a negative charge of two or more, such as molybdate and tungstate, the metalate anion may be associated with only one electropositive complexing site. Typically, the metalate loaded support comprises, as determined by conventional elemental analysis, at least about 0.1, and preferably at least about 1, say, about 2 to 30, e.g., about 5 to 25, weight percent of the metal of the metalate (metal basis) based on total weight of the dry support. The saturation of the electropositive complexing sites of the insoluble support is the only limitation upon the maximum weight percent of metalate contained in association with the electropositive complexing sites on the insoluble support. It is generally desired to achieve as close to saturation levels as possible for reasons of activity and life.

DISCUSSION OF THE PRODUCTION OF ALKYLENE GLYCOLS

Vicinal alkylene oxides which may be used to produce alkylene glycols have the general formula:

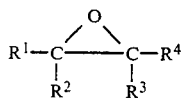

wherein $R^1$, $R^2$, and $R^3$ and $R^4$ are the same or different and are hydrogen or hydrocarbyl-containing substituents of 1 to about 20 carbon atoms. Often $R^1$, $R^2$, $R^3$ and $R^4$ are hydrogen, alkyl of between 1 and about 10 carbons, monocyclic or bicyclic aryl having up to about 12 carbons alkaryl having 7 to about 10 carbons, monocyclic or bicyclic aralkyl having 7 to about 15 carbons, alkenyl having 2 to 3 carbons, cycloalkyl having 3 to about 8 carbons, and cyclic structures joining two of $R^1$, $R^2$, $R^3$ and $R^4$ having 3 to about 8 carbon atoms. Representative of alkylene oxides are ethylene oxide, propylene oxide, butylene oxide, including isobutylene oxide, 1,2-butylene oxide and 2,3-butylene oxide, pentylene oxide, styrene oxide, cyclohexene oxide and the like. Preferably, the alkylene oxide is an aliphatic alkylene oxide having 2 or 3 carbon atoms, i.e., ethylene oxide and propylene oxide.

Alkylene oxides are well known, as is their preparation. For example, alkylene oxide can be prepared by reacting an olefin with an organo hydroperoxide in the presence of a catalyst or by the partial oxidation of ethylene with a molecular oxygen-containing gas in the presence of a silver catalyst. Frequently, the alkylene oxide has been purified to avoid the presence of components which may produce troublesome impurities in the alkylene glycol product from the hydrolysis.

Water is also employed as a reagent for the formation of the corresponding alkylene glycol and is preferably provided as a liquid although steam may be used. Usually the water is of sufficient purity to provide a suitable quality alkylene glycol product. The water may be distilled or demineralized, for example, by ion exchange treatment.

The mole ratio of water based on the alkylene oxide as provided to the reaction zone is generally at least about 0.1. However, it is desirable to maintain at least a slight molar excess of water over the amount of water required for reaction with the alkylene oxide on a stoichiometric basis to ensure a higher selectivity of alkylene oxide to the monoalkylene glycol product. The mole ratio may be greater than 50, but such high ratios often prove to be commercially unattractive because of the energy required to recover the alkylene glycol. Typically, the mole ratio of water to alkylene oxide is between about 1:1 and 40:1, say between about 1:1 and 30:1 and, when high selectivities to the monoalkylene product are desired, the ratio is preferably at least about 5:1 to 30:1.

It is believed that the hydrolysis reaction in the processes of this invention can proceed by at least two routes, one involving the selectivity-enhancing metalate and the other being the conventional route. Thus, the processes of this invention are capable of producing dialkylene glycol and higher glycols. Hence, the lower the ratio of water to alkylene glycol, all other factors remaining the same, the greater the amount of these dialkylene and higher glycols that will be produced. This provides a degree of flexibility in operating processes of the invention to provide a desired amount of these higher glycols but an amount less than would be obtained in a conventional process. In most instances, the mole ratio is in the range of about 3:1 to 10:1; however, for two-step processes, lower mole ratios are frequently preferred, say, about 1:1 to 5:1.

Another factor affecting the degree of selectivity to the monoalkylene glycol is the amount of metalate anion employed. Generally, the greater the amount of metalate anion employed, the higher the selectivity to monoalkylene glycol, all other factors remaining the same. Thus, the mole ratio of metalate anion to alkylene oxide may be up to 5:1 or 10:1 or more. Economics usually dictate that the mole ratio of metalate anion to alkylene oxide will be less than about 2:1. Often, the mole ratio is at least about 0.001:100, say, in the range of about 0.05:100 to 2:1, e.g., about 0.1:100 to 1:1, and most frequently about 1:100 to 0.5:1. In two-stage processes, mole ratios of metalate anion to alkylene oxide are often closer to those required for complete association of the alkylene oxide with the metalate anion in order to ensure substantially 100 percent selectivity to the monoalkylene glycol. When using a solid containing metalate anion in association therewith, the availability of metalate anion sites may be restricted. Thus, greater ratios of metalate anion to alkylene oxide are preferred, say, about 0.01:1 to 20:1, e.g., about 0.05:1 to 15:1.

Hydrolysis conditions which favor the conventional hydrolysis route can also be avoided. Most notably, the pH of the reaction menstruum can be maintained relatively neutral so as to avoid the acidic and basic conditions which have a significant promotional effect on the conventional hydrolysis rate. Typically, the pH is maintained between about 5 and 11, preferably about 6 to 10.5, and most often the pH is in the range of about 6 to 10.

With some metalate anions, such as the vanadates, tungstates and molybdates, the pH of the medium can be determinative of the specie present. For example, in strong bases the orthovanadate may predominate, but at neutral conditions metavanadate will exist. In another example, more acidic media promote the formation of polynuclear molybdates which often have less, if any, beneficial effect in enhancing selectivity.

The pH may be maintained within the desired range by the addition of acid or base, or the addition of buffers, as is well known in the art; however, the presence and nature of salts should be considered since displacement of the metalate anion from the electropositive complexing site can occur resulting in the loss of the metalate anion. Mechanisms which have been proposed for maintaining the desired pH include the addition of carbon dioxide or inorganic acids or organic acids such as sulfuric acid, hydrochloric acid and acetic acid. The agents for maintaining the pH value of the reaction menstruum may be added in any convenient manner such as during the reaction, e.g., by purging with carbon dioxide, or by addition to one or more of the reactants prior to introducing the reactants into the reactor. For example, the pH of the water component may be adjusted to the desired level prior to admixing with the alkylene oxide.

The maintenance of the pH within the desired ranges can also have a secondary effect of enhancing the stability of the association between the metalate and the electropositive complexing site, and enhancing the stability of the solid support, e.g., anion exchange resin. Thus, even brief excursions into high pH ranges, e.g., pH values greater than 11, should generally be avoided.

The process is carried out at temperatures sufficient to enable the selectivity-enhancing effect of the metalate anion to be achieved. The benefits of the metalate anion are believed to be achievable at low temperatures, but the rate of production of alkylene glycol may be undesirably low. The temperature, however, should not be so high that the organometalate is unduly adversely affected. Accordingly, the process is often carried out at a temperature between about 20° C. and about 200° C. With the use of many anion exchange resins, temperatures greater than about 140° C. or 150° C. are generally avoided because of potential deterioration of the pendant active groups. Most often, the reaction is carried out at a temperature between about 50° C. and 140° C., say, about 80° C. to 130° C. or 140° C. when using these anion exchange resins.

In accordance with the processes of this invention, the stability of the organometalate is believed to be enhanced by the addition of small quantities of metalate anion to the reaction mixture. This metalate anion is believed to replace any metalate anion lost from the organic-containing cation during the course of the reaction. Often, the amount of metalate anion provided can be relatively small, e.g., less than 1,000 ppm by weight based on the reactants fed to the reaction zone, say, about 1 to 1000, e.g., about 5 to 250, ppm by weight. Often, the mole ratio of metalate anion added to the metalate anion in association with the electropositive complexing sites is less than 1:10, say, 0.001:100 to 1:20.

The metalate anion-containing material used as the stabilizing material is preferably more soluble in water than the organometalate. Thus, the cation of the stabilizing material is able to migrate in the aqueous phase and, if it donates a metalate anion to the organic-containing cation, it can become associated with another anion and be removed from the system with the glycol product. Most preferably the stabilizing material is relatively soluble in water, e.g., at least about 50 grams of the stabilizing material can be dissolved in a liter of water at 25° C.

The metalate anion may be provided as any convenient, dissociatable metalate anion-containing material. Thus, the metalate anion-containing material is frequently a water soluble acid or salt, i.e., the cations include hydrogen, alkali metals, alkaline earth metals, ammonium ion, copper, zinc, iron, quaternary ammonium cations, quaternary phosphonium cations, sulfonium cations, and the like. Conveniently, the cation is sodium or potassium due to its ready availability. However, in some instances it is desirable to employ an organic-containing cation, e.g., containing up to about 6 carbon atoms in each hydrocarbyl-containing substituent, to facilitate its separation from the alkylene glycol product by extraction into a water-immiscible phase in which it is preferentially soluble. See for further discussion U.S. patent application Ser. No. 594,266, filed on even date herewith, of B. T. Keen, et al., herein incorporated by reference.

The metalate anion need not be the same as the metalate anion initially in association with the electropositive complexing sites; however, the initial metalate anion will tend to be replaced by the metalate anion added. Consequently, the metalate anion added is usually the same as the initial metalate anion.

The pressure may be subatmospheric, atmospheric or above atmospheric. The process is usually carried out at a pressure sufficient to maintain the reactants in the liquid phase. For purposes of convenience, the reaction is typically conducted at pressures greater than ambient, e.g., between about 0.1 and 1,000 kilograms per square centimeter gauge and preferably between about 2 and 100 kilograms per square centimeter gauge.

The production of alkylene glycol according to this invention may be conducted in the presence of a gas, which is preferably inert. Gases which may be employed include air, carbon dioxide, nitrogen, argon and the like. Carbon dioxide is often present during the hydrolysis of alkylene oxide by the very nature of the process and the source of the alkylene oxide (especially ethylene oxide by partial oxidation of ethylene). Frequently, it is desired to maintain the mole ratio of carbon dioxide to alkylene oxide less than 0.1:1, particularly less than about 0.05:1. Carbon dioxide can be used in certain amounts to enhance the selectivity provided by vanadate anion such as disclosed in U.S. patent application Ser. No. 594,265, filed on even date herewith, of B. T. Keen, herein incorporated by reference.

The process may be conducted in the presence of a solvent which does not unduly adversely affect the organometalate, alkylene oxide or alkylene glycol. Interactive solvents such as 1,2-dimethoxyethane may find use.

Most frequently when using a two-step or two-phase (liquid) hydrolysis system, the organometalate is provided in a solvent which is substantially immiscible with water. Exemplary of liquid solvents are alkyl, cycloalkyl and aromatic-containing solvents, especially halogenated alkyl, cycloalkyls and aromatics, such as cyclopentane, cyclohexane, methylcyclohexane, cycloheptane, benzene, toluene, xylene, naphthene, dichloromethane, 1,1,2-trichloroethane and the like. Not all the above solvents will be suitable for all of the processes of this invention.

The amount of solvent, when employed, can vary widely and is frequently in the range of about 0.1:1 to 10:1 volumes per volume of water. The amount of solvent employed is often determined based upon the solubility of the metalate anion-containing material in the solvent, whether the substantially water-insoluble phase is to be the continuous phase, the desired mass for the dissipation of heat from the exothermic reaction, and the like.

A two-phase process may be conducted in any suitable manner for reactions in menstruum containing more than one phase. For instance, the aqueous phase may provide the continuous phase or the substantially water-insoluble phase may be the continuous phase. In general, it is desired that the discontinuous phase is highly dispersed and is in the form of small bubbles to enhance the interface areas between the phases. For example, the discontinuous phase can have bubble diameters of less than about 2, say, less than about 1, e.g., about 0.01 to 0.5, centimeters. Devices to enhance the dispersion may be employed such as agitators, spargers and the like may thus find application. However, in order to obtain an enhanced selectivity to monoalkylene glycol, it is not usually essential to have a dispersed phase. Indeed, the phases may form adjacent layers during conducting the reaction.

The relative amounts of the aqueous phase and the substantially water-insoluble phase may vary widely, for instance, from 1000:1 to 1:1000 on a volume basis. Usually, the amount of the aqueous phase is selected in respect to the amount of alkylene oxide employed in the process since it is a reactant and must be separated from the alkylene glycol products.

The process of the invention may be carried out as a batch reaction or as a continuous process. Conventionally, hydrolysis processes for the manufacture of alkylene glycols are conducted on a continuous basis, and the processes of this invention are particularly adapted to such continuous operation. In such operations, the alkylene oxide and water reactants, which may or may not be previously admixed, are introduced into a reactor which may be maintained under isothermal, adiabatic or hybrid conditions. The hydrolysis reaction is exothermic, and hence, the temperature of the incoming reactants and the heat transfer abilities from the reactor affect the temperatures achieved within a reactor. Similarly, the unreacted and excess reactants and other components of the reaction medium, such as solvents, serve as a heat sink. Conventional hydrolysis reactors are substantially adiabatic and enable high temperatures for evaporating water for the recovery of alkylene glycol to be achieved. Since it may be beneficial from the standpoint of maintaining the stability of the metalate anion association, the electropositive complex sites and the support, isothermal reactors may be preferred. Moreover, since the constant temperature used in an isothermal reactor can be greater than the inlet temperature to an adiabatic reactor, the amount of metalate anion required may be less than that required in an adiabatic reactor.

Generally, the reaction is conducted for a period of time sufficient to ensure that substantially all the alkylene oxide is reacted. The amount of time required to accomplish the substantially complete reaction is determined by the other conditions employed including temperature, amount of reactants present, and the like. The reaction may be carried out for very short periods of time, e.g., fractions of a second, and if desired may be carried out for periods of up to hours. Alternatively, the hydrolysis may occur in several zones, all of which contain the metalate-containing solid support of this invention.

The alkylene glycol may be recovered from the reaction effluent in any convenient manner. Typically, the water is removed in a series of multiple-effect evaporators and the alkylene glycol is further refined by vacuum distillation.

Preferably, metalate anion moieties (the organometalate and/or the added metalate anion-containing material) are also separated from the glycol-containing hydrolysis product. The separation techniques are advantageously selected with consideration to providing an integrated process for making alkylene glycols from alkylene oxides. For example, the separation may be effected by phase separation when a water-immiscible solvent is employed and the solvent selected is a better solvent for the metalate anion moieties than water but is a worse solvent than water for alkylene glycol. With solid organometalates, the alkylene glycol can be separated as the liquid phase after, e.g., settling or filtration. Also, metalate-containing material can be extracted from the alkylene glycol-containing phase by contact with an immiscible liquid in which the metalate anion or its associated cation is preferentially soluble. See, for example, copending U.S. patent application Ser. No. 594,266, filed on even date herewith, of B. T. Keen, et. al., herein incorporated by reference. Alternatively, the alkylene glycol containing medium may be contacted with, for instance, an anion exchange resin such as a chloride-loaded DOWEX TM MSA-1 available from The Dow Chemical Company resin to recover the metalate anion. This resin can be separated and regenerated with the metalate anion being returned to the associated moiety-forming stage. The alkylene glycol can be recovered and refined in a suitable manner. See for further discussion U.S. patent application Ser. No. 594,269, filed on even date hereinwith, of J. A. Collier, herein incorporated by reference. It is also possible to recover the metalate anion-containing material by distillation (e.g., evaporation or fractional distillation) from the alkylene glycols. When employing higher temperature separation processes, e.g., above about 100° to 120° C., the provision of small amounts of water enhances the stability of many metalate anions.

The following examples are provided to assist in the understanding of the invention and are not in limitation thereof. All percentages and parts of solid are by weight and all percentages and parts of liquids and gases are by volume, unless otherwise indicated.

In the following examples, the below described analytical method was used to determine alkylene glycol products in samples from reaction effluents. The samples were prepared by adding about 2 weight percent 1,3-butanediol as an internal standard. Approximately 50 microliters of this admixture were added to 1.0 milliliter of Regisil TM silane, i.e., (BSTFA) N,N-bis trimethylsilyl trifluoroacetamide, available from the Regis Chemical Company, Morton Grove, Ill., in a serum vial and mixed for at least about 12 hours. The weight percent monoethylene glycol, diethylene glycol and triethylene glycol were determined by standard vapor phase chromatography using a Hewlett Packard 5880 TM gas chromatograph equipped with a 4 meter by ⅛ inch (0.32 centimeters) (outside diameter) stainless steel column packed with 20 percent OV-101 methyl silicone stationary liquid phase supported on 80–100 mesh Chromosorb W HP TM available from Supelco, Inc., Bellefonte, Pa.

The selectivity to each glycol component is calculated as the quotient of the weight percent of the subject glycol divided by the sum of the weight percents of each of the monoethylene glycol, diethylene glycol and triethylene glycol.

EXAMPLES 1 TO 5

These experiments were carried out in a U-shaped ⅜" (0.95 cm) (outside diameter) stainless steel reactor. Generally, the reactor was charged from both ends with the desired volume of resin as a slurry in water. The volume of wet resin charged to the reactor as well as the reactor length are as listed in Table 1. The resin was held in place by stainless steel frits placed at each end of the bed. Chilled (5° C.) water, ethylene oxide and alkali metalate (when employed) were charged into a feed tank (internal volume 900 cc) and kept pressurized at 25 pounds per inch gauge pressure with nitrogen. Stainless steel tubing (1/16") (0.16 cm) carried the reactants from the feed tank to the reactor and the products from the reactor to the product receiver. A back pressure regulator was used to keep the system pressure at 200 pounds per inch gauge pressure (nitrogen). The flow of reactants to the reactor was controlled by a dual piston high pressure liquid chromatography pump (Altex 100A pump—now owned by Beckman Instruments). The reaction products were cooled to ambient temperature by immersing a coiled section of a reactor exit line in a water bath. The U-shaped reactor was immersed (typically only to the level of the resin in the reactor) in a stirred constant temperature oil bath.

Conversion of the alkylene oxide was 100 percent except where noted and monoalkylene glycol selectivities are as shown in Table 1. The anion exchange resin catalysts were prepared using aqueous solutions of the designated alkali metal metalate. In all instances, the chloride concentration of the wash effluent after the exchange with the metalate anion was less then about 5 ppm as determined by ion chromatography. The general preparation procedure was to suspend the resin in an aqueous solution of the metalate (e.g. about 5 wt. percent) at room temperature with stirring for about one-half hour, wash, and repeat contact with the metalate by eluting an aqueous solution of the metalate through a glass column packed with the resin until the chloride was completely exchanged. The resin was then thoroughly washed with water.

the liquid, the resin was loaded into a glass column (about 2.5 centimeters in diameter) and about 1.5 liters of an aqueous solution containing three weight percent sodium molybdate was pumped through the column at a relatively low rate (in the neighborhood of 5 milliliters per minute).

The resin was employed for the hydrolysis of ethylene oxide using an apparatus such as described in respect to Examples 1 to 5. The reactor length was about 33 centimeters with the resin loosely packed therein. Glass wool was placed between the resin bed and each of the frits to prevent plugging the frits. The solution for feeding to the reactor contained about 1800 grams of water, 180 grams of ethylene oxide and about 0.6 grams of sodium molybdate. The rate of feed was varied from about 0.2 to 1.0 milliliter per minute. The reactor was maintained at about 125° C., and pressure of about 14 atmospheres gauge. At a feed rate of about 0.2 milliliters per minute, the conversion of ethylene oxide was substantially complete, and the product was analyzed for selectivity to monoethylene glycol which was about 93 percent.

TABLE I

| Ex. | REACTANT SOLUTION | | | Resin Type/ Metalate Loaded | Volume Wet Resin in Reactor (cc) | Approximate Reactor Length (cm.) | Flow Rate ml/min. | Reaction Temp. °C. | Monoalkylene Glycol Selectivity % |
|---|---|---|---|---|---|---|---|---|---|
| | Alkylene Oxide/Wt. % | Water (Wt. %) | Alkali Metalate/ppm wt. | | | | | | |
| 1 | EO/9.2 | 90.8 | $Na_2MoO_4$/6 | DOWEX MSA-1/ $MoO_4^{-2}$ | 15 | 33 | 1.0 | 146 | 98.4 |
| 2 | EO/10.1 | 89.9 | $Na_2MoO_4$/140 | DOWEX MSA-1/ $MoO_4^{-2}$ | 15 | 33 | .72 | 152 | 96.7 |
| 3 | EO/7.7 | 92.3 | $Na_2WO_4$/102 | DOWEX MSA-1/ $WO_4^{-2}$ | 19.5 | 43 | 1.0 | 131 | 98.2 |
| 4 | EO/20.0 | 80.0 | $Na_2WO_4$/170 | DOWEX MSA-1/ $WO_4^{-2}$ | 19.5 | 43 | .80 | 135 | 94.1 |
| 5 (comparative) | EO/12.5 | 87.5 | None | DOWEX MSA-1/ $V_2O_7^{-4}$ | 14.5 | 33 | 1.00 | 121 | 97.9 |

EO = Ethylene oxide

EXAMPLE 6

Into a glass vessel was charged 400 grams of an aqueous solution (about 15 wt. %) of Cat-Floc TM T-1 polymer available from Calgon, Inc., having an average molecular weight of about 300,000 and heterocylic nitrogen which is a quaternary ammonium group in association with chloride anion. About 1600 milliliters of water were added to the solution followed by about 80 milliliters of wet DOWEX MSC-1 TM cationic exchange resin having sulfonic functionality available from The Dow Chemical Company. The mixture was stirred at a temperature of about 50° C. overnight. The liquid was decanted and 1200 milliliters of water and 400 grams of the aqueous solution containing Cat-Floc T-1 TM polymer was added. The mixture was stirred while heating at about 70° to 80° C. for approximately five hours. The liquid was decanted and another mixture was formed with 1200 milliliters of water and heated to about 70° to 80° C. for five hours with stirring. The liquid was decanted and the solid resin was washed twice with 500 milliliters of water.

The metalate was incorporated into the resin by slurrying it in about one liter of an aqueous solution containing about five weight percent of sodium molybdate. This slurry was heated to about 50° C. for 3 hours while stirring. the liquid was decanted and this slurrying process was conducted two more times. After decanting

EXAMPLE 7

About 50 grams of Davison 59 TM silica gel available from Davison Chemical Division of W. R. Grace Co. (about 8 to 20 mesh U.S. Sieve Series), were charged to a 500 milliliter glass erlenmeyer flask and 253 grams of a solution of 2 parts by weight of concentrated hydrochloric acid to one part by weight of water were added. A condenser (water-cooled) was placed on the flask. The solution was refluxed for three hours and the liquid decanted. The solids were washed three times with water and placed in a glass column having a diameter of about 2.5 centimeters and length of about 70 centimeters. Water was then pumped through the silica gel bed until the pH was in the range of about 6 to 7 (approximately 4 liters of water). About 500 milliliters of methanol were provided to the column to dehydrate the silica gel, and the solids were recovered but maintained covered with methanol.

The acid activated silica gel was separated from the methanol by decanting, and it was placed with 300 milliliters of toluene into a previously dried, 500 milliliter round bottom flask. The flask was purged with nitrogen, equipped with a condenser and then heated to reflux. About 35 milliliters of overhead (as a liquid) were recovered. The mixture was cooled to about 60° C. and 8.6 grams of (N,N-dimethyl-3-amino)propyl trimethoxysilane were added dropwise to the solution. The solution was then refluxed overnight and about 10 milliliters of overhead material was collected. After cooling to about 60° C., another 8 grams of the silane were added dropwise and the solution was refluxed for four hours and cooled to about 60° C. About one milliliter of water was added and the solution was again refluxed overnight. After cooling to about 60° C., about 5 grams of the siloxane were added and the solution was refluxed for about four hours. After cooling to about 60° C., one milliliter of water was added and the solution was refluxed overnight. The solution was then cooled and filtered to recover the solids which were then dried for about one hour at 150° C. Analysis indicated that the silica gel had about 1.21 meq/g of amine sites.

Approximately 30 grams of the silica gel having the amine sites were charged with about 100 milliliters of 1,2-dimethoxyethane into a stirred, round bottom flask. To this mixture was added 15 milliliters of a previously prepared solution containing 10 milliliters of iodomethane and 5 milliliters of 1,2-dimethoxyethane. The mixture was allowed to stand overnight and then, with stirring, another 5 milliliters of iodomethane were added, and the mixture was heated to about 60° C. It was then cooled and the solids recovered by filtration and washed with water. The washed solids were placed in a glass column having a diameter of about 2.5 centimeters and a length of about 45 centimeters.

About two liters of an aqueous solution containing about 60 grams of sodium molybdate were slowly pumped (about 3 to 5 milliliters per minute) through the column at a temperature of about 80° C. The solids were again washed and then vacuum dried. Elemental analysis revealed that the solids contained about 1.46 percent molybdenum.

This material was used for the hydrolysis of ethylene oxide using an apparatus such as described in respect to Examples 1 to 5. The reactor length was about 33 centimeters with the resin loosely packed therein. Glass wool was placed between the bed and the frits. The solution used for the hydrolysis contained about 1800 milliliters of water, about 180 milliliters of ethylene oxide and about 0.25 grams of sodium molybdate. The rate of feed was varied between about 1.0 and 0.5 milliliters per minute. The reactor was maintained at about 125° C. under a pressure of about 14 atmospheres gauge. At a feed rate of about 0.5 milliliters per minute, the conversion of ethylene oxide was substantially complete and the selectivity to monoethylene glycol was about 95 percent. After about one and one-half days the pressure increased and the reactor was shut down. The solids bed had compressed and fines were observed.

EXAMPLE 8

Into an erlenmeyer flask were added about 76 grams of 20 weight percent aqueous solution of Cat-Floc T-1 ™ polymer and about 100 grams of Ludox HS-40 ™ colloidal silica available from E. I. duPont de Nemours & Co., Inc. A precipitate immmediately formed. The slurry was heated at about 70° to 80° C. for two hours while stirring. The liquid was then decanted, water added to form another slurry, and the slurry heated at about 70° to 80°. This procedure was repeated several times. Then the solids were again slurried in water and the pH adjusted to about 7 with molybdic acid. The solution was again heated to about 60° to 80° C. for thirty hours.

The solid was recovered by filtration and placed in a glass column (about 2.5 centimeters diameter) and a dilute aqueous solution of sodium molybdate was passed through the column until virtually no chloride was detected in the eluant.

The solids were then recovered and employed for the hydrolysis of ethylene oxide using an apparatus such as described in respect to Examples 1 to 5. About 6.6 grams of the solids (dry) were loosely packed in a reactor about 25 centimeters in length. Water was pumped through the reactor to expel air and glass wool placed between the solids and frits. The feed mixture to be used contained about 1800 milliliters of water, about 180 milliliters of ethylene oxide and about 0.25 grams of sodium molybdate. The rate of feed was varied from about 0.3 to 1.0 milliliters per minute. The temperature of the reactor was maintained at about 125° C. with a pressure of about 14 atmospheres gauge. At a feed rate of about 0.33 milliliters per minute, the conversion of ethylene oxide was substantially complete and the selectivity to monoethylene glycol was about 95 to 96 percent. When the temperature was increased to about 140° C. with a feed rate of about 0.5 milliliters per minute, the conversion remained substantially complete but the pressure increased and the selectivity was about 94 percent. The reactor was shut down and, upon inspection, the frit on the outlet side of the reactor was plugged.

It is claimed:

1. A process for making alkylene glycols from alkylene oxide and water comprising contacting the alkylene oxide and water in a hydrolysis zone in the presence of a water-insoluble phase, said water-insoluble phase containing a selectivity-enhancing amount of a dissociatable organometalate having an organic-containing cation and a selectivity-enhancing metalate anion, said contacting being under hydrolysis conditions sufficient to form alkylene glycol, and separating the substantially water-insoluble phase wherein a stability enhancing amount of stabilizing material having a cation and a selectivity-enhancing metalate anion is provided to the hydrolysis zone, said stabilizing material being soluble in water.

2. The process of claim 1 wherein the organometalate comprising a solid having electropositive complexing sites thereon.

3. The process of claim 2 wherein the organometalate comprises anion exchange resin.

4. The process of claim 1 wherein the organometalate is dissolved in a water-immiscible solvent and is preferentially soluble in the water-immiscible solvent as compared to water.

5. The process of claim 4 wherein the organometalate comprises a cation represented by the formula:

$$[(R^0)_m Y_n]^{x+}$$

wherein Y is a polyvalent element which is an ionic charge carrying center; $R^0$ is hydrogen or hydrocarbyl-containing substituent with the proviso that Y has at least one $R^0$ which contains a hydrocarbyl substituent; m is the average number of electron pairs shared by Y with the total $R^0$ groups; and n is the number of charge carrying centers, wherein m, n and x are related by the equation $x = n(V - m)$ in which V is the average functional oxidation state of Y wherein each electron pair used by each Y in bonding to R is given the value of 1 and the functional oxidation state of Y is the sum of the electron pairs bonding to $R^0$ and x/n, and x is an integer of 1 or 2.

6. The process of claim 1 wherein said stabilizing material comprises an ammonium or alkali metal metalate.

7. The process of claim 2 wherein said stabilizing material comprises an ammonium or alkali metal metalate.

8. The process of claim 5 wherein said stabilizing material comprises an ammonium or alkali metal metalate.

9. A continuous process for making alkylene glycols from alkylene oxide and water comprising (a) continuously providing to a hydrolysis zone alkylene oxide and water, said hydrolysis zone containing an aqueous phase and a water-insoluble phase containing a selectivity-enhancing amount of a dissociatable organometalate having an organic-containing cation and a selectivity-enhancing metalate anion, said hydrolysis zone being maintained under hydrolysis conditions sufficient to form alkylene glycol;

(b) feeding to the hydrolysis zone an amount of stabilizing material sufficient to enhance the stability of the organometalate, said stabilizing material having a cation and a selectivity-enhancing metalate anion and being soluble in water;

(c) separating the water-insoluble phase from the aqueous phase from the hydrolysis zone, said aqueous phase containing alkylene glycol and cation of the stabilizing material.

10. The process of claim 9 wherein the mole ratio of metalate anion of the stabilizing material to metalate anion of the organometalate is about 0.001:100 to 1:20.

11. The process of claim 10 wherein the metalate anion of the stabilizing material is the same as the metalate anion of the organometalate.

12. The process of claim 11 wherein metalate anion is represented by the structure:

$[(A)_m M(O)]^{-q}$ wherein M is a polyvalent metal atom having a positive functional oxidation state of at least +3, q is the negative charge of the metalate anion, and A is one or more substituents to fill the remaining valencies (m) of M and is selected from the group consisting of double-bonded oxygen and —O— wherein at least one A is —O—.

13. The process of claim 12 wherein the metalate anion comprises at least one of molybdate, tungstate, hydrogen pyrovanadate and pyrovanadate.

14. The process of claim 13 wherein the alkylene oxide has the formula

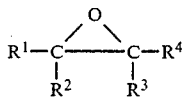

wherein $R^1$, $R^2$, $R^3$ and $R^4$ are the same or different and are hydrogen, alkyl of between 1 and 10 carbon atoms, monocyclic and bicyclic aryl having up to about 12 carbon atoms, alkaryl having about 7 to 10 carbon atoms, monocyclic or bicyclic aralkyl having 7 to about 15 carbon atoms, alkenyl having 2 or 3 carbon atoms, cycloalkyl having 3 to about 8 carbon atoms, and cyclic structures joining two of $R^1$, $R^2$, $R^3$ and $R^4$ having 3 to about 8 carbon atoms.

15. The process of claim 13 wherein the alkylene oxide is ethylene oxide.

16. The process of claim 15 wherein the organometalate comprises a solid having electropositive complexing sites thereon.

17. The process of claim 16 wherein the electropositive complexing sites are represented by the structure $[-X-(R)_n]^+$ wherein X is nitrogen, phosphorous, sulfur, or arsenic bonded directly or indirectly to the support, each R may be the same or different and is hydrogen, monocyclic aryl or aralkyl of 6 to 8 carbon atoms, monocyclic aralkyl of 7 to 9 carbon atoms, or alkyl or alkoxy of 1 to about 6 carbon atoms and n designates that sufficient R groups are provided to satisfy the remaining valencies of X.

18. The process of claim 17 wherein each R is alkyl.

19. The process of claim 17 wherein each R is methyl.

20. The process of claim 17 wherein X is attached to the solid support through an alkylene, arylene, silyl or siloxy group.

21. The process of claim 17 wherein the electropositive complexing sites comprise protonated tertiary amine.

22. The process of claim 17 wherein the electropositive complexing sites comprise quaternary phosphonium.

23. The process of claim 17 wherein the electropositive complexing sites comprise quaternary ammonium.

24. The process of claim 17 wherein the cation of the stabilizing material comprises ammonium or alkali metal ion.

25. The process of claim 15 wherein the water-insoluble phase is a liquid phase.

26. The process of claim 25 wherein the organometalate comprises a cation represented by the formula:

$[(R^0)_m Y_n]^{x+}$ wherein Y is a polyvalent element which is an ionic charge carrying center; $R^0$ is hydrogen or hydrocarbyl-containing substituent with the proviso that Y has at least one $R^0$ which contains a hydrocarbyl substituent; m is the average number of electron pairs shared by Y with the total $R^0$ groups; and n is the number of charge carrying centers, wherein m, n and x are related by the equation x=n(V−m) in which V is the average functional oxidation state of Y wherein each electron pair used by each Y in bonding to R is given the value of 1 and the functional oxidation state of Y is the sum of the electron pairs bonding to $R^0$ and x/n, and x is an integer of 1 or 2.

27. The process of claim 26 wherein the water-insoluble phase comprises solvent.

28. The process of claim 27 wherein the solvent comprises at least one of benzene, toluene, xylene, dichloromethane and 1,1,2-trichloroethane.

29. The process of claim 28 wherein the cation of the organometalate comprises quaternary ammonium.

30. The process of claim 27 wherein the cation of the stabilizing material comprises ammonium or alkali metal ion.

* * * * *